US012636465B2

(12) United States Patent
Chueh et al.

(10) Patent No.: US 12,636,465 B2
(45) Date of Patent: May 26, 2026

(54) BALLOON-FREE, SELF-RETAINABLE AND THREADABLE URETHRAL CATHETER

(71) Applicant: National Taiwan University, Taipei City (TW)

(72) Inventors: Jeff Shih-Chieh Chueh, Taipei City (TW); Chi-An Dai, Taipei City (TW)

(73) Assignee: NATIONAL TAIWAN UNIVERSITY, Taipei City (TW)

( * ) Notice: Subject to any disclaimer, the term of this patent is extended or adjusted under 35 U.S.C. 154(b) by 245 days.

(21) Appl. No.: 18/720,379

(22) PCT Filed: Dec. 8, 2023

(86) PCT No.: PCT/US2023/083113
§ 371 (c)(1),
(2) Date: Jun. 14, 2024

(87) PCT Pub. No.: WO2024/124126
PCT Pub. Date: Jun. 13, 2024

(65) Prior Publication Data
US 2025/0082894 A1 Mar. 13, 2025

Related U.S. Application Data

(60) Provisional application No. 63/431,030, filed on Dec. 8, 2022.

(51) Int. Cl.
*A61M 25/00* (2006.01)
*A61M 25/01* (2006.01)

(52) U.S. Cl.
CPC .... *A61M 25/0017* (2013.01); *A61M 25/0045* (2013.01); *A61M 25/0068* (2013.01); *A61M 25/0074* (2013.01); *A61M 25/0102* (2013.01); *A61M 2025/0008* (2013.01); *A61M 2205/0216* (2013.01); *A61M 2205/0238* (2013.01);
(Continued)

(58) Field of Classification Search
CPC .......... A61M 25/0017; A61M 25/0045; A61M 25/0068; A61M 25/0074; A61M 25/0102
See application file for complete search history.

(56) References Cited

U.S. PATENT DOCUMENTS

| | | | | |
|---|---|---|---|---|
| 4,871,356 | A * | 10/1989 | Haindl | A61M 25/00 604/537 |
| 6,171,230 | B1 * | 1/2001 | Hakky | A61F 2/0009 600/29 |

(Continued)

*Primary Examiner* — Guy K Townsend
(74) *Attorney, Agent, or Firm* — WPAT, PC

(57) ABSTRACT
The present disclosure provides a balloon-free, self-retainable and threadable urethral catheter that contains special external markings to guide insertion, and that could be indwelled easily and safely. Through various experiments and the structural configuration, the balloon-free, self-retainable and threadable urethral catheter of the present disclosure can make insertion of a mushroom-tip urethral catheter easily performed by primary care medical professionals, instead of previously only been done by senior urologists with a semi-rigid stainless-steel stylet. This disclosure leads to better urine drainage and reduces irritation to the posterior wall of the bladder. With the special design of this disclosure, minor urethral structure can be overcome to insert this catheter safely.

8 Claims, 21 Drawing Sheets

(52) U.S. Cl.
CPC ................. *A61M 2205/583* (2013.01); *A61M 2210/1085* (2013.01); *A61M 2210/1089* (2013.01)

(56)                    References Cited

U.S. PATENT DOCUMENTS

| | | | | |
|---|---|---|---|---|
| 6,283,940 B1 * | 9/2001 | Mulholland | ...... | A61M 25/0075 |
| | | | | 606/198 |
| 6,364,855 B1 * | 4/2002 | Zappala | ............... | A61N 5/1027 |
| | | | | 604/48 |
| 9,498,596 B1 * | 11/2016 | Hakky | .............. | A61M 25/0905 |
| 2002/0045886 A1 * | 4/2002 | Porter | ............... | A61M 25/0017 |
| | | | | 604/104 |
| 2002/0143292 A1 * | 10/2002 | Flinchbaugh | ..... | A61M 25/0075 |
| | | | | 604/107 |
| 2012/0179145 A1 * | 7/2012 | Nishtala | ........... | A61M 25/0017 |
| | | | | 604/544 |
| 2013/0218101 A1 * | 8/2013 | Wake et al. | .......... | A61M 25/01 |
| | | | | 604/267 |
| 2019/0366046 A1 * | 12/2019 | Klocke | .............. | A61M 25/1011 |
| 2024/0399120 A1 * | 12/2024 | Donahue | ............... | A61L 29/146 |
| 2025/0082894 A1 * | 3/2025 | Chueh | .............. | A61M 25/0068 |

* cited by examiner

| Formulation ratio (A:glycerol) | 20:1 | 20:2 | 20:3 | 20:4 |
|---|---|---|---|---|
| Thickness (μm) | 200 | 160 | 180 | 160 |
| Swelling time | 6 min | 3 min 30 s | 1min | 30s |
| Dissolved time | 18 min | 13 min | 11 min | 10min |

FIG. 5

| Formulation ratio (A:glycerol) | 20:1 | 30:2 | 20:2 |
|---|---|---|---|
| Thickness (μm) | 200 | 160 | 160 |
| Swelling time | 6 min | 4 min | 3 min |
| Dissolved time | 19 min | 16 min | 10 min |

Transparent and soft

Suitable swelling time and dissolved time

FIG. 6

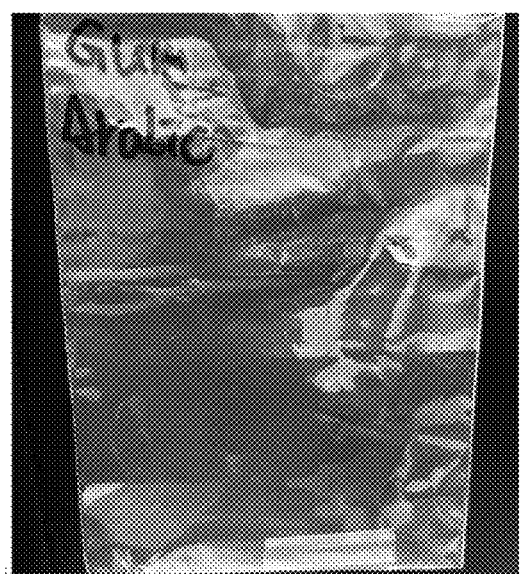
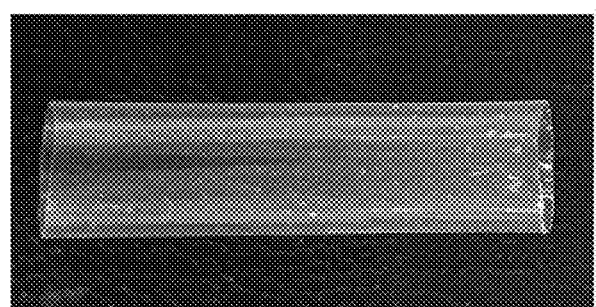
FIG. 7
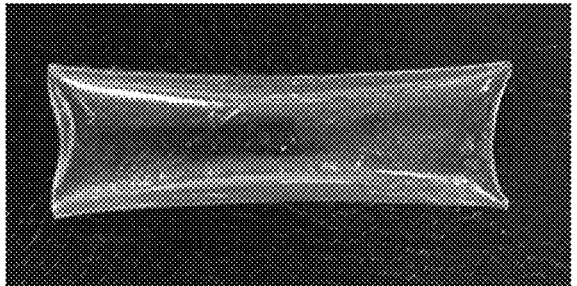
FIG. 8

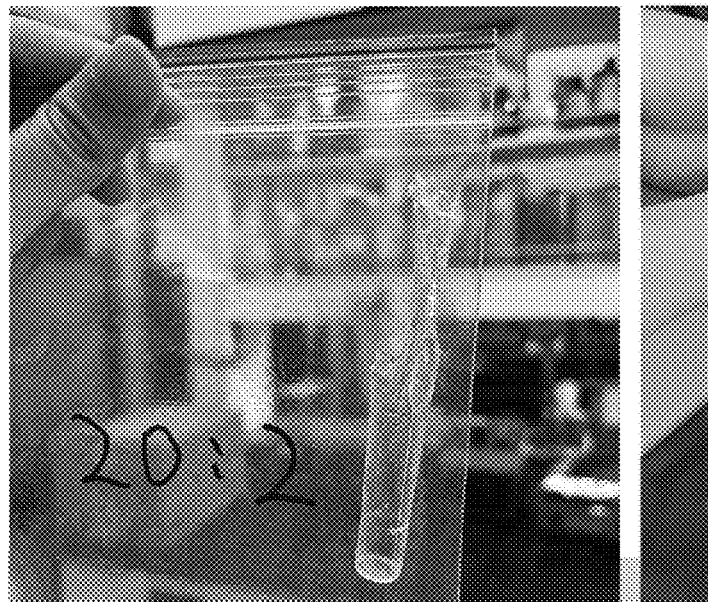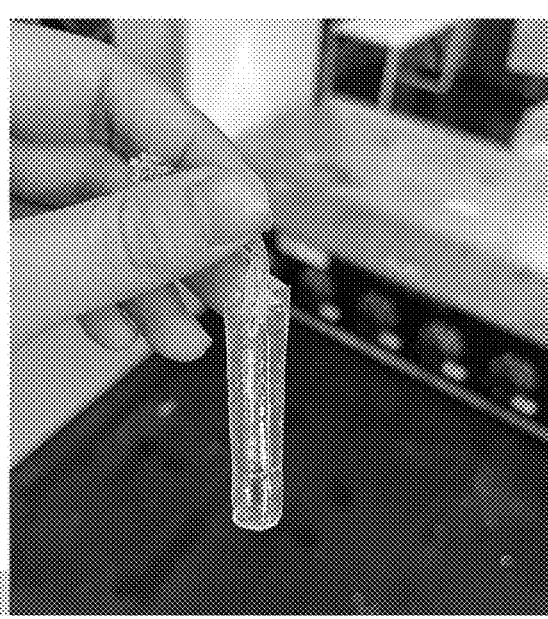
FIG. 9
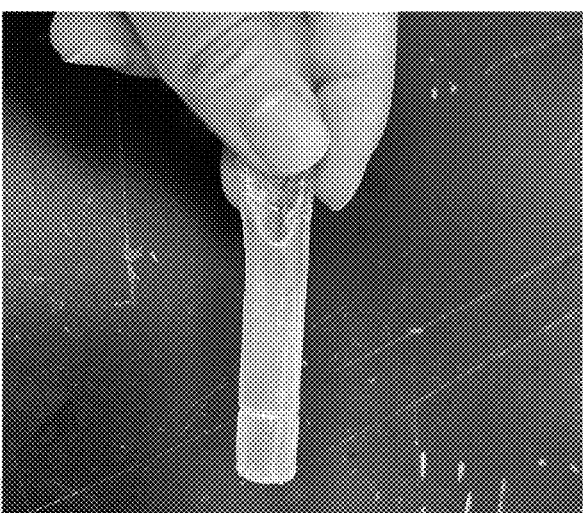
FIG. 10

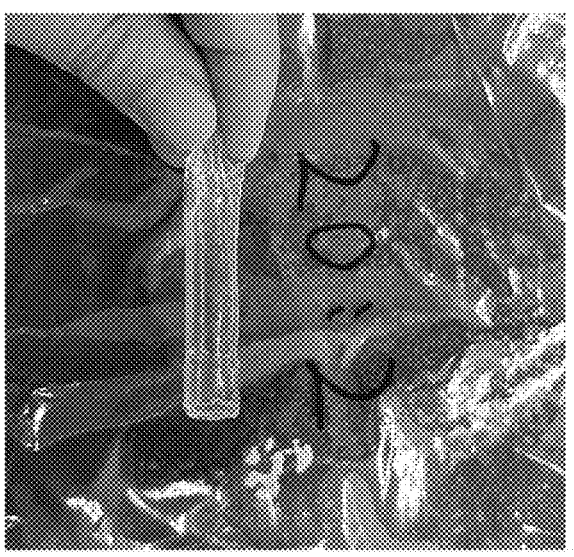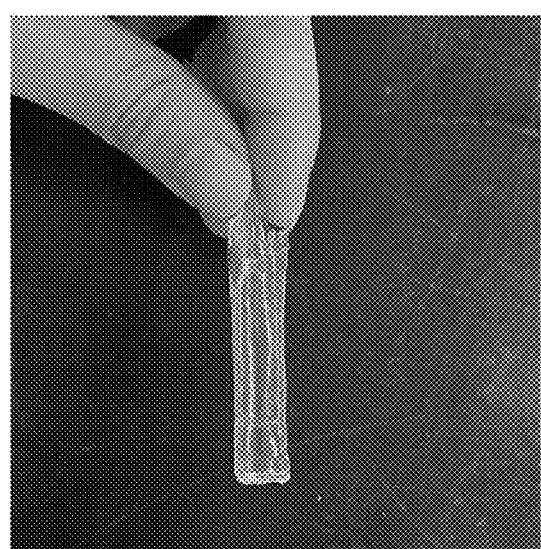
FIG. 11
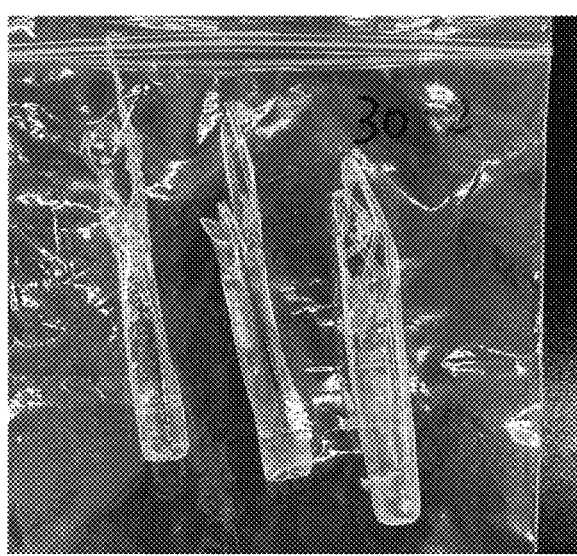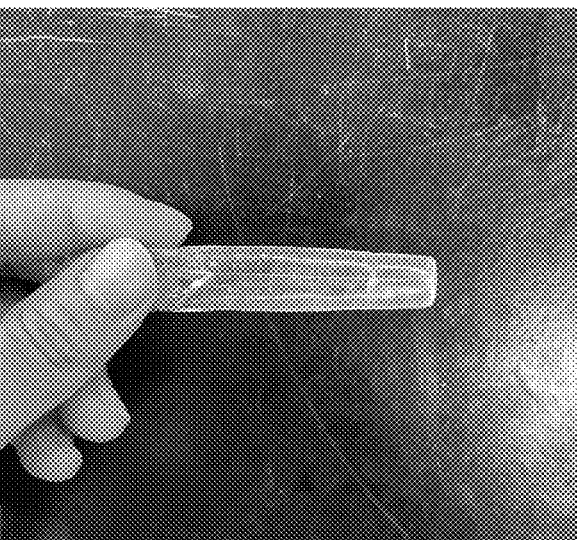
FIG. 12

Before drying
After drying
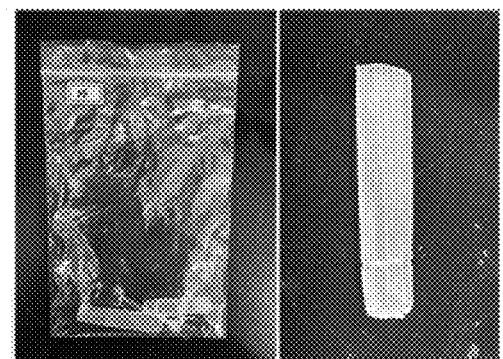 
FIG. 13

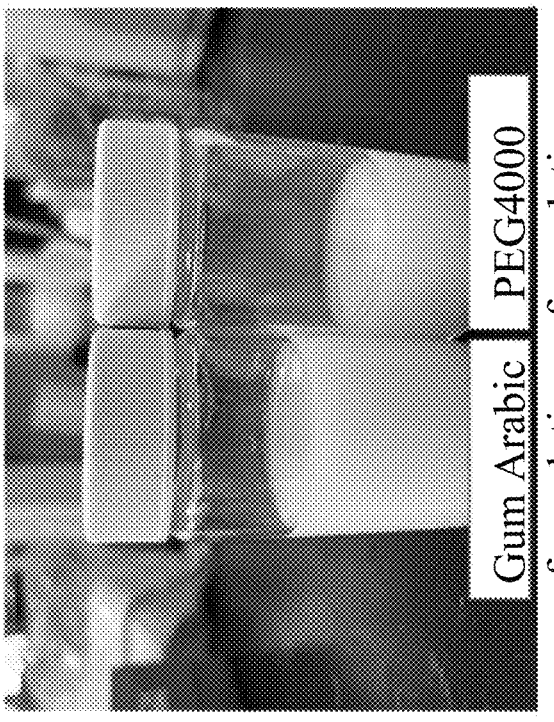
FIG. 14

PEG4000 formulation
Gum Arabic formulation
FIG. 15

1

2

1

2

1

2

10                   The Solution

Meet the *Duette*™

Preventing Bladder Trauma

While Dr. Witta was collecting images of bladder trauma through cystoscopy, he noticed that unlike the dome of the bladder, where the catheter tip and drainage eyes make contact with the bladder walls, the neck of the bladder, where the retention balloon of the Foley rests on the bladder walls, showed no signs of trauma to the bladder wall or to the protective mucosal layer. This led him to design a new catheter, one with a distal balloon that would subsume the catheter tip and help keep the drainage eyes from aspirating the walls of the bladder.

The result of this work is the *Duette*™, the world's first twin-balloon, zero-tip catheter.

How it Works

By subsuming the tip and expanding the surface area over which the bladder collapses, the *Duette's*™ second distal balloon prevents the tip from eroding and penetrating the bladder's mucosal lining. Additionally, the proximal and distal balloons create a standoff, preventing the bladder wall from getting close enough to the drainage eyes to sustain aspiration damage.

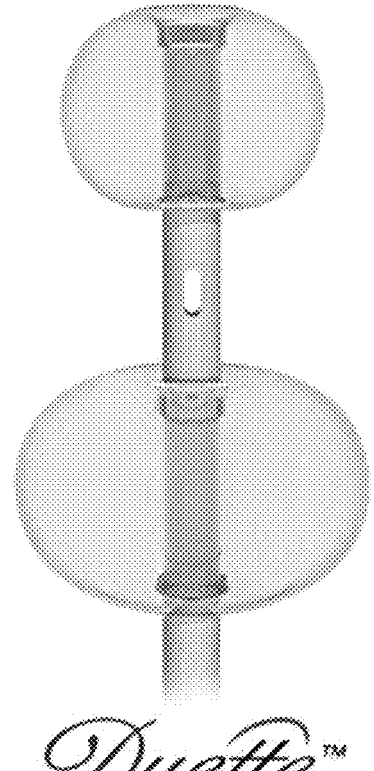

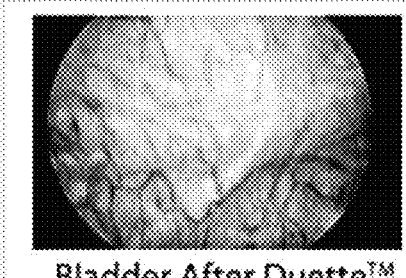

Bladder After Duette™

The *Duette*™ is also functionally equivalent to a standard Foley catheter, requiring only one additional step (the inflation of the distal balloon) be performed during catheterization. As a result, it requires minimal additional training for nurses and doctors to use safely and effectively.

*Duette*™

FIG. 22

BALLOON-FREE, SELF-RETAINABLE AND THREADABLE URETHRAL CATHETER

CROSS-REFERENCE TO RELATED APPLICATION

This application claims priority of Provisional application No. 63/431,030, filed on Dec. 8, 2022, the content of which is incorporated herein in its entirety by reference.

BACKGROUND OF THE INVENTION

1. Field of the Invention

The present invention relates to a balloon-free, self-retainable and threadable urethral catheter that contains special external markings to guide insertion, and that could be indwelled easily and safely.

2. The Prior Art

Urethral catheter is a medical device frequently used clinically. According to the International Society for Infectious Disease, more than 100 million urethral catheters are used worldwide each year, and 20% of hospitalized patients in the United States use urethral catheters. However, the balloon-type urethral catheters that are common in clinical practice today are often accompanied by possible complications such as cystitis, urinary tract stones, and urinary retention. In addition to increasing patient discomfort, hospitalization days and medical expenses may also be increased, and the burden on the medical system is increased.

The insertion process of traditional competing products on the market today is relatively unsafe. In addition to requiring a urological specialist to place it, it also requires the use of a built-in metal stylet, which may harm the urethra and cause urethral trauma. Other competing products (e.g.: Lotus) do not require the use of additional metal stylet; yet, the internal catheter of Lotus cannot be removed, which may affect the patency of urine drainage. If there are blood clots or impurities in the patient's urine, there is a higher possibility of catheter obstruction.

Except for Duette™ (see FIG. 22), Lotus catheter (see FIG. 23) and Flume catheter (FIG. 24), there are few corresponding novel medical devices. Except the above-mentioned ones, the majorities of the existing urethral catheters have been used in medical practice for decades. Even if they are not ideal, few people have made serious efforts to develop a new, nearly ideal product.

The material of the modified Malecot catheter and its internal stylet (if present) as well as the various new designs needs to be soft and flexible after assembly (i.e.: the final product inserted into the urethra). The stiffness of the novel urethral catheter cannot be harder than the currently used balloon catheter to avoid urethral injury and urethral false-way; so as to ensure the safety of urethral catheter insertion.

Current Malecot catheters do not have a built-in locking mechanism between the stainless steel stylet and the catheter; requiring considerable urological expertise and experience to install it correctly. The force required by the operator to hold a stylet in place for insertion is also relatively challenging to master and increases the risk of mechanical error, patient discomfort due to manipulation, trauma, and/or creation of false passages.

In order to solve the above-mentioned problems, those skilled in the art urgently need to develop a novel balloon-free, self-retainable and threadable urethral catheter for the benefit of a large group of people in need thereof.

SUMMARY OF THE INVENTION

A primary objective of the present invention is to provide a balloon-free, self-retainable and threadable urethral catheter that contains special external markings to guide insertion, and that could be indwelled easily and safely. It comprises a catheter, including a proximal flexible mushroom-like winged end and a distal end relative to the proximal flexible mushroom-like winged end, wherein the catheter has a hollow inner lumen between the proximal flexible mushroom-like winged end and the distal end; and a stylet, if present, movably inserted into the hollow inner lumen of the catheter from the distal end; wherein the proximal flexible mushroom-like winged end conforms longitudinally when force is applied, and forms a contour with its diameter larger than an outer diameter of the catheter when the force of the stylet is not applied.

According to an embodiment of the present invention, the balloon-free, self-retainable and threadable urethral catheter could further comprise an external adhesive or a wrapping material, wherein the external adhesive or the wrapping material wraps the proximal flexible mushroom-like winged end of the catheter to keep the proximal flexible mushroom-like winged end in a straight streamline form for easy passage through the urethra.

According to an embodiment of the present invention, the external adhesive or the wrapping material is a water-soluble coating or a water-soluble capsule shell made of special water-soluble materials.

According to an embodiment of the present invention, the water-soluble coating or the water-soluble capsule shell comprises a formulation solution, and the formulation solution comprises a special water-proof emulsion.

According to an embodiment of the present invention, the water-proof emulsion consists of hydrophilic monomers and lipophilic monomers.

According to an embodiment of the present invention, the balloon-free, self-retainable and threadable urethral catheter further comprises a water-soluble coating and/or a capsule shell surrounding the proximal flexible mushroom-like winged end of the catheter, making it streamlined and can be easily inserted through the urethra and into the bladder. The water-soluble coating would be dissolved in the urine in 2-3 minutes of initiating the act of insertion, and then the dissolved fragments would be discharged from the catheter.

According to an embodiment of the present invention, the balloon-free, self-retainable and threadable urethral catheter could further comprise a locking mechanism, wherein the locking mechanism includes a threaded nut and a bolt segment matching the threaded nut, and the bolt segment is disposed on the stylet.

According to an embodiment of the present invention, the catheter further includes a grip, and the grip is disposed at the distal end.

According to an embodiment of the present invention, the catheter and the stylet are made of flexible materials.

According to an embodiment of the present invention, a small hole is formed at the proximal flexible mushroom-like winged end, and the small hole and the hollow inner lumen form a continuous space to allow a guidewire to pass through.

According to an embodiment of the present invention, the distal end is formed with an external opening, the balloon-free, self-retainable and threadable urethral catheter further comprises a detachment mechanism, and the detachment mechanism is located at the external opening.

According to an embodiment of the present invention, the proximal flexible mushroom-like winged end includes a multi-winged mushroom portion, the stylet pushes and streamlines the catheter and makes the multi-winged mushroom portion straightened in a pre-assembled unpackaged form.

According to an embodiment of the present invention, the distal end and the stylet near the distal end are formed with an external opening, and the external opening is provided with a click and lock mechanism or a snap-on closing mechanism.

According to an embodiment of the present invention, the proximal flexible mushroom-like winged end becomes streamlined when force is applied.

According to an embodiment of the present invention, the stylet has a proximal tip that meets the proximal flexible mushroom-like winged end of the catheter when inserted into the hollow inner lumen of the catheter.

According to an embodiment of the present invention, the catheter further includes a ruler marking disposed on the catheter, the ruler marking includes male ruler markings (blue) and female ruler markings (red) respectively, and the ruler marking is used to notify users of different genders regarding the length of the catheter already inserted into the body.

In summary, through various experiments and the structural configuration, the balloon-free, self-retainable and threadable urethral catheter of the present invention can improve the efficiency of urine drainage from the urinary bladder and can make insertion of a mushroom-tip urethral catheter easily performed by primary care medical professionals, instead of previously only been done by senior urologists with a semi-rigid stainless-steel stylet. This disclosure leads to better urine drainage and reduces irritation to the posterior wall of the bladder. With the special design of this disclosure, minor urethral structure can be overcome to insert this catheter safely.

BRIEF DESCRIPTION OF THE DRAWINGS

The following drawings form part of the present specification and are included here to further demonstrate some aspects of the present invention, which can be better understood by reference to one or more of these drawings, in combination with the detailed description of the embodiments presented herein.

FIG. 5 shows the trends in different ratios of urethral catheter capsule formulations.

FIG. 6 shows the determination of the final ratio of hydrophilic polyethylene glycol (PEG) added to the glycerol formulation.

FIG. 7 shows the finished gum arabic formulation.

FIG. 8 shows the finished hydrophilic polymer PEG and glycerol formulation.

FIGS. 9-13 show the storage status of finished urethral catheter capsules.

FIGS. 14 and 15 show the storage status of the observed solution samples.

FIG. 22 shows a schematic diagram of the Duette™ catheter.

DETAILED DESCRIPTION OF THE PREFERRED EMBODIMENT

Figure 1:
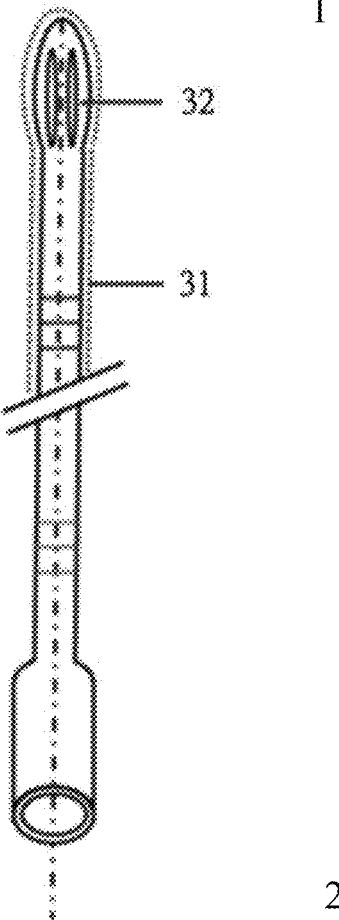
FIG. 1 illustrates a side view of an assembled catheter (with a streamlined design holding the proximal winged portion snugly enclosed within a soluble wrap), according to one embodiment of the present invention.
Figure 2:
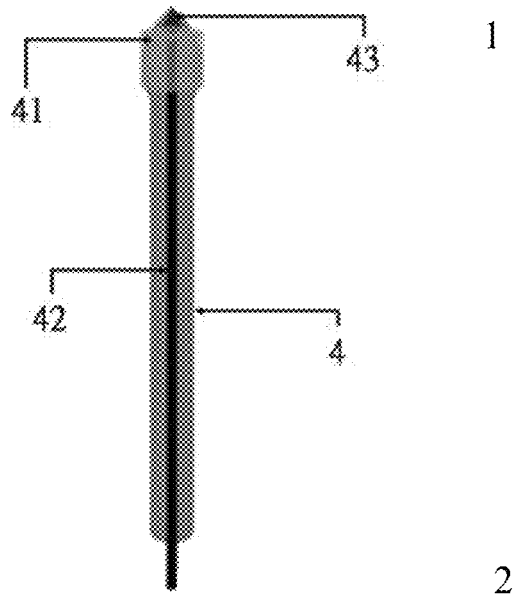
FIG. 2 illustrates the water-soluble coating wrapping at the proximal "winged tip" of the catheter. The coating will dissolve and the catheter will return to its multi-winged shape to keep this catheter in the bladder from spontaneous dislodgement when exposed to water or urine.

In the following detailed description of the embodiments of the present invention, reference is made to the accompanying drawings, which are shown to illustrate the specific embodiments in which the present disclosure may be practiced. These embodiments are provided to enable those skilled in the art to practice the present disclosure. It is understood that other embodiments may be used and that changes can be made to the embodiments without departing from the scope of the present invention. The following description is therefore not to be considered as limiting the scope of the present invention.

Definition

As used herein, the data provided represent experimental values that can vary within a range of ±20%, preferably within ±10%, and most preferably within ±5%.

Unless otherwise stated in the context, "a", "the" and similar terms used in the specification (especially in the following claims) should be understood as including singular and plural forms.

Most importantly, the main thesis of this invention is "easy and safe insertion of an proximal mushroom-like indwelling urethral catheter" that would change the preference, and thus the routine medical practice, of the majority of the indwelling urethral catheters from the current urethral catheters containing a water balloon at its proximal tip to this modified novel catheter.

Maybe some of the ideas mentioned below have been used in similar catheters, but the fact is currently in the market there is no such modified novel balloon-free self-retainable thread-able urethral catheter I described, and the Malecot catheter is rarely used in the clinical practice mainly due to the possible challenges that could be encountered during its insertion. With the applicant's multiple modifications and innovations, the assembled composite end result is that this new catheter provides simpler, safer, while allowing flexible alternative technique of urethral catheter insertion.

Example 1

FIGS. 1-4 illustrate a urethral catheter in accordance with an embodiment of the present disclosure. The characteristic of this embodiment is to use some external adhesive or wrapping material 31 (FIG. 1) to keep the proximal winged portion 32 (FIG. 1) of the winged-fenestrated balloon-free urethral catheter in the straight streamline form, and once the catheter is in position, some special mechanism will be activated to release the winged portion from the constraint and to assume its anchoring function of the catheter. The mechanisms of activation under consideration are like some temperature-sensitive water-soluble or urine-soluble biodegradable wraps (polyvinyl alcohol (PVA, PVOH), polyvinylpyrrolidone (PVP), or medical-grade wafer paper; RESOMER® Biodegradable Polymers like PLA); or it could also be some temperature-sensitive water-soluble or urine-soluble biodegradable adhesives that could hold the winged portion 32 (FIG. 1) together during production, but the adhesives between the wings dissolve and activate the anchoring mechanism while that portion of the catheter is inserted into the body and is in contact with the urine; or the mechanism could be activated by pulling a thread hidden in the lumen of the pre-packaged catheter.

Figure 3:
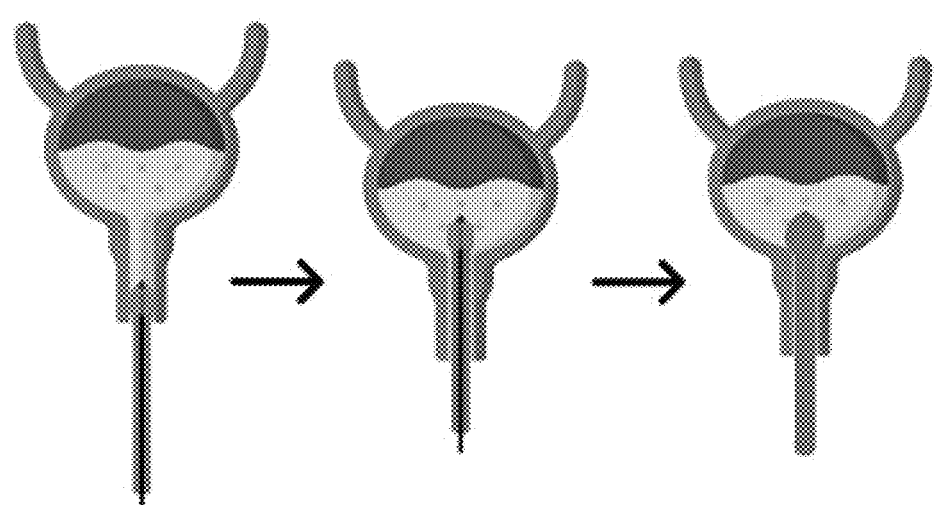
FIG. 3 illustrates the process of spontaneous expansion of the proximal end of a catheter that remains wrapped in a water-soluble coating to prevent its spontaneous deployment.
Figure 4:
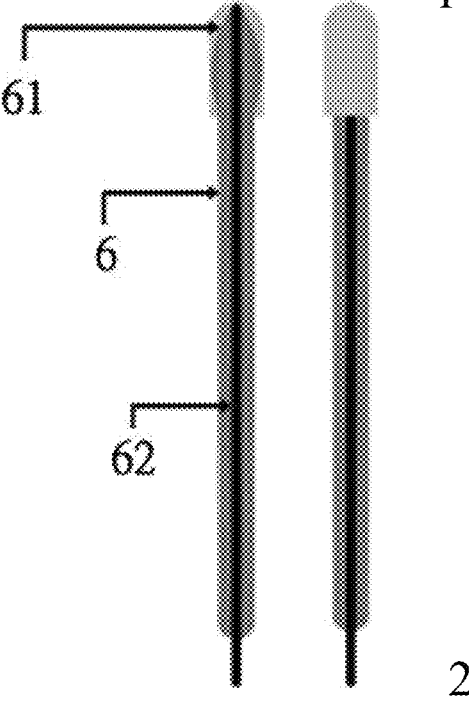
FIG. 4 illustrates the water-soluble capsule shell at the proximal "winged tip" of the catheter. The capsule shell will dissolve and the catheter will return to its multi-winged shape to keep this catheter in the bladder from spontaneous dislodgement when exposed to water or urine.

Other ideas include a soft and water-soluble coating 41 (see FIG. 2) that is made of water-soluble material (such as PVA), wrapping at the proximal "winged (or mushroom-like) tip" of the catheter 4. The coating or capsule shell 41 (FIG. 2) will be strong enough to make the proximal apart maintain a similar diameter as the other part of the catheter. In order to make the catheter pass the unitary tract smoothly, a stylet 41 (FIG. 2) that is harder than the catheter will be glued to the top of the catheter by water-soluble glue. And the glue 43 (FIG. 2) will dissolve in the urine within a quick period of time and then discharge from the catheter. Then the catheter will return to its multi-winged shape to keep this catheter in the bladder from spontaneous dislodgement (FIG. 3).

In addition, another example we proposed is that the water-soluble capsule shell 61 (FIG. 4) will be made of water-soluble material (such as PVA). The winged (or mushroom-like) tip of the catheter 6 will be bound by water-soluble wire. The water-soluble wire will be strong enough to make the proximal apart maintain a similar diameter as the other part of the catheter. This method can turn the front end of the catheter into a blind pipe, which does not require the use of water-soluble glue to stick the stylet 62 (FIG. 4), and also prevents the stylet from running out from the front end and hurting human tissues during the entry process. In addition, making it into a capsule shape will make the contact surface with the catheter relatively smooth. Then the catheter will return to its multi-winged shape to keep this catheter in the bladder from spontaneous dislodgement.

Example 2

The capsule formulation of the urethral catheter contains gelatin in the prior art (PVA:gelatin:water-proof emulsion=14:1:3). Gelatin is a thermoreversible gel derived from animal gum. It is soft, non-toxic and easily soluble. Gelatin easily causes the dip-coating solution to settle, which is not conducive to the manufacturing process. Taking into account that after being sold as a product, there will be people of various religions, the animal formulation is removed. Therefore, the gelatin formulation is directly replaced, and the following experiments are performed. Experiment 1: The final weight ratio of hydrophilic PEG added to the glycerol formulation is determined. Experiment 2: The storage condition of finished urethral catheter capsules is observed. Experiment 3: The storage status of solution samples is observed.

First, the trends of different weight ratios are observed. The formulation solution of PVA:PEG4000:water-proof emulsion=14:1:3 is called A. The result is shown in FIG. 5. As the amount of glycerol added increases, the swelling time and dissolved time decrease.

Experiment 1: The final weight ratio of hydrophilic PEG added to the glycerol formulation is determined. The formulation solution of PVA:PEG4000:water-proof emulsion=14:1:3 is called A. The result is shown in FIG. 6.

Next, the gelatin formulation is directly replaced, see Table 1.

TABLE 1

| formulation | Gum Arabic | PEG + glycerol (*20:2) |
|---|---|---|
| thickness (μm) | 140 | 160 |
| swelling time | 2 min 12 s | 3 min |
| dissolved time | 13 min | 10 min |

*The formulation solution of PVA:PEG4000:water-proof emulsion = 14:1:3 is called A (A:glycerol = 20:2).

These two sets of formulations having suitable swelling time and dissolved time when directly replacing gelatin are confirmed. These two sets of formulations were sent to the Plastic Center for asking to help make urethral catheter capsules for subsequent testing. It was delivered at room temperature, hoping to improve the previous foaming process.

FIG. 7 shows the finished gum arabic formulation sent back by the Plastic Center. FIG. 8 shows the finished hydrophilic polymer PEG and glycerol formulation sent back by the Plastic Center.

Experiment 2: The storage condition of finished urethral catheter capsules is observed. After production, finished urethral catheter capsules were placed in a ziplock bag and stored in a drying oven. After a week of observation, it is found that the formulation of hydrophilic PEG and glycerol is easy to absorb moisture (see FIGS. 9-13, in which A:glycerol=20:2 in FIGS. 9 and 11, A:glycerol=30:2 in FIGS. 10 and 12). As can be seen from FIGS. 11 and 12, after half an hour of drying in the oven, the transparency would return to normal, and the moisture-absorbing condition can be restored to the original state through post-processing. FIG. 13 shows the finished gum arabic formulation. After production, it was stored in a drying oven and observed after 23 days. There was no obvious difference from before drying.

Experiment 3: The storage status of solution samples is observed. The prepared sample solution was stored in a dark place at room temperature for one month and then observed. There was no obvious sedimentation. Stir was performed just a little before making the coating (see FIG. 14). As can be seen from FIG. 15, there is no mold to the naked eye, but we still need to consider whether to add preservatives, such as phenoxyethanol. From the above results, it is determined that the optimal weight ratio of the hydrophilic PEG formulation is A:glycerol=20:2, wherein the formulation solution of PVA:PEG4000:water-proof emulsion=14:1:3 is called A. The formulation of hydrophilic PEG and glycerol is easy to absorb moisture, and the subsequent packaging process requires vacuum drying. The plant-based formulation and hydrophilic polymer PEG formulation can be stored in a dark place at room temperature without settling, and there is no mold problem observed with the naked eye.

The measurement methods of swelling time and dissolved time are as follows. Swelling time: Squeeze a pea-sized amount of jelly onto gauze, rub it on the coated urethral catheter and start timing. Dissolved time: Cut the coating into small pieces, start timing when immersed in water, and stop timing when about 80% is dissolved in the water.

Example 3

Figure 16:
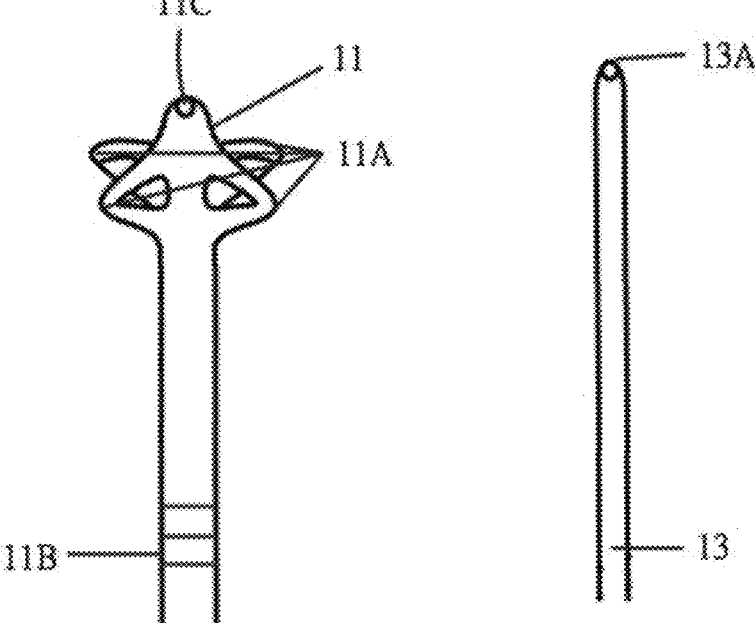
FIG. 16 illustrates the separated internal soft stylet and external catheter, the external catheter includes a flexible winged portion, and the flexible winged portion forms a contour larger than an outer diameter of the external catheter when a force is not applied.
Figure 17:
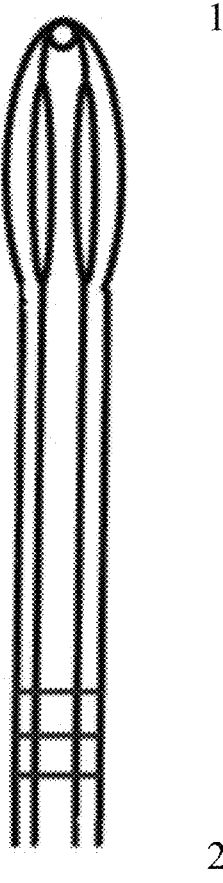
FIG. 17 illustrates a side view of an assembled proximal bladder portion of the balloon-free self-retainable thread-able externally calibrated urethral catheter (FIG. 16), according to one embodiment of the present invention. The flexible winged portion conforms longitudinally when force is applied.

FIGS. 16 and 17 illustrate a urethral catheter in accordance with an embodiment of the present disclosure. The flexible internal stylet 13 is inserted into the catheter 11. The catheter 11 includes a proximal end 1 of a flexible winged portion 11A and a distal end 2 relative to the proximal end 1 of the flexible winged portion 11A. The catheter 11 has a hollow inner lumen between the proximal end 1 of the flexible winged portion 11A and the distal end 2; the proximal tip 13A of the stylet 13 (firmer than the material of the external actual catheter; having a small knob to avoid the stylet 13 pushing through the hole 11C (closest to the proximal end of the catheter) for the guidewire at the proximal tip of the urethral catheter) meets the internal proximal tip of the catheter. The catheter 11 further includes a ruler marking 11B disposed on the distal end, and the ruler marking 11B is used to notify as to the length of the catheter already inserted into the body. The flexible winged portion 11A conforms longitudinally along the catheter 11 when force is applied (see FIG. 17), forms a streamlined linear shape, and forms a contour larger than an outer diameter of the catheter 11 when the force is not applied (see FIG. 16).

Example 4

Figure 18:
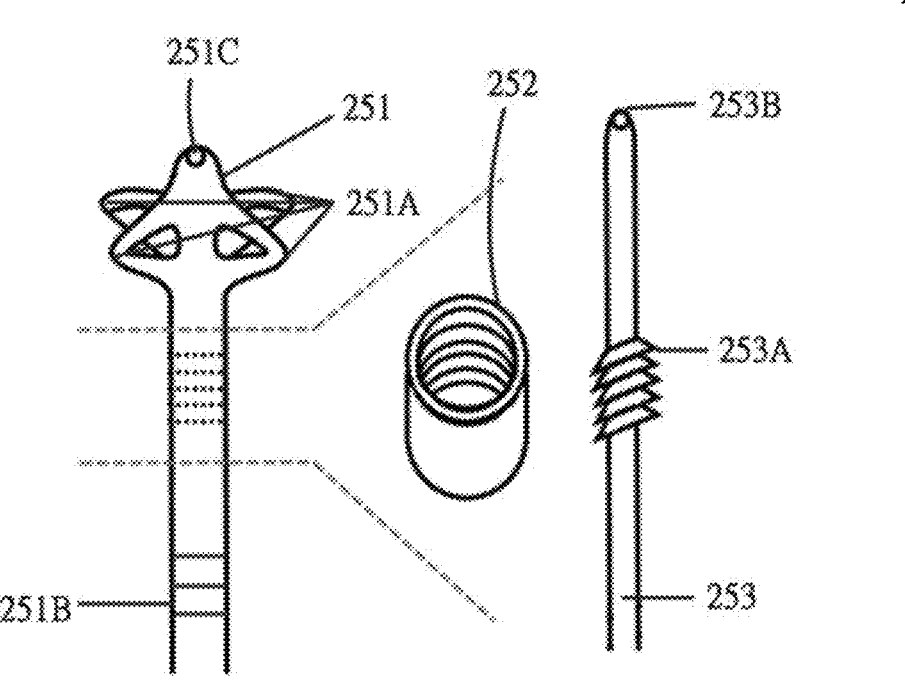
FIG. 18 illustrates the separated internal soft stylet and external catheter with dissected "bolt and nut" mechanism of the proximal bladder portion of the balloon-free self-retain-able thread-able externally calibrated urethral catheter, according to one embodiment of the present invention.
Figure 19:
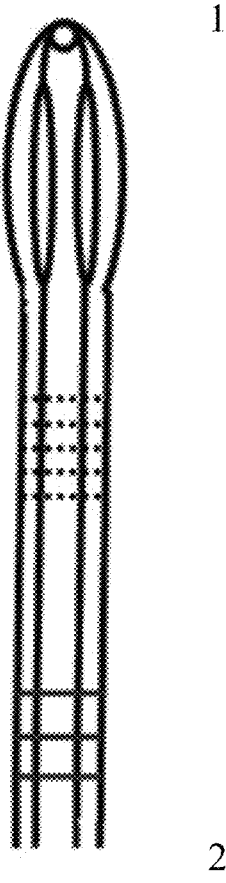
FIG. 19 illustrates a side view of an assembled proximal bladder portion of the balloon-free self-retainable thread-able externally calibrated urethral catheter (FIG. 18), according to one embodiment of the present invention.

FIGS. 18 and 19 illustrate a urethral catheter in accordance with an embodiment of the present disclosure. A flexible internal stylet 253 is inserted into the catheter 251, with the proximal tip 253B of the stylet 253 (firmer than the material of the external actual catheter; having a small knob to avoid the stylet 253 pushing through the hole 251C for the guidewire at the proximal tip of the urethral catheter) meeting the internal proximal tip of the catheter, locked in and holding the streamlined linear shape of the winged tip (see FIG. 19); i.e.: the catheter 251 and the stylet 253 are already assembled together with all the wings straighten for immediate insertion when the product is unpackaged.

The locking mechanism is achieved by a short threaded nut-and-bolt segment and on the corresponding surfaces (external for the stylet 253; i.e.: bolt 253A, and internal for the catheter; i.e.: nut 252) of each component, presumably near the beginning of the winged proximal tip 251A of the catheter and fastened to extension, in order to straighten and streamline the winged portion of the catheter, so that the winged fenestrations of the external catheter could be straightened into stream-line design with a longer part of the internal stylet 253A-B proximal to the nut-and-bolt screwing mechanism; to facilitate easy passage of this portion of the catheter through the urethral lumen.

Once the catheter is inserted into the patient's bladder to a satisfactory depth (suggested by the female ruler markings 251B (FIG. 18) or 271B (FIG. 20), and male ruler markings 271C (FIG. 20)) on the external surface of the winged-fenestrated balloon-free urethral catheter), the inner stylet is unfastened via counter-clock wise rotation of a grip 273 on the distal end 2 of the component, extending beyond the length of the catheter.

Sufficient rotation of the stylet dis-engages the nut 272 and bolt 273A threaded locking mechanism of the device, returning the winged tip of the catheter to its pre-manufactured relaxed state 271A, the notification markers 251B over the proximal end of the stylet could be seen; allowing the stylet to be removed easily. The urethral catheter 251 is gently pulled back until some mild resistance is met; indicating the winged proximal 251A end of the catheter is located at the bladder neck, thus reducing the risk of accidental catheter removal. Furthermore, a pre-attached catheter fixation pad to fix the external part of the catheter to the nearby body surface to prevent inadvertent dislodgement of the catheter is secured by the provider at this time.

To emphasize a few more details of the components mentioned above briefly: 1. Both catheter 251 and stylet 253 components are hollow in length and made of flexible materials except for the harder segments with threaded surfaces; 2. As the proximal end 1 of the device will be out of sight for the user upon insertion, ruler markings 251B/ 271B/271C on the exterior surface of the catheter notifies the operator as to the length of the device already inserted into the patient, which may assist in the process of inserting the winged tip past the bladder neck; this improves the accessibility and accuracy of the device insertion, and avoids traumatizing the posterior bladder wall with the assembled catheter.

Figure 20:
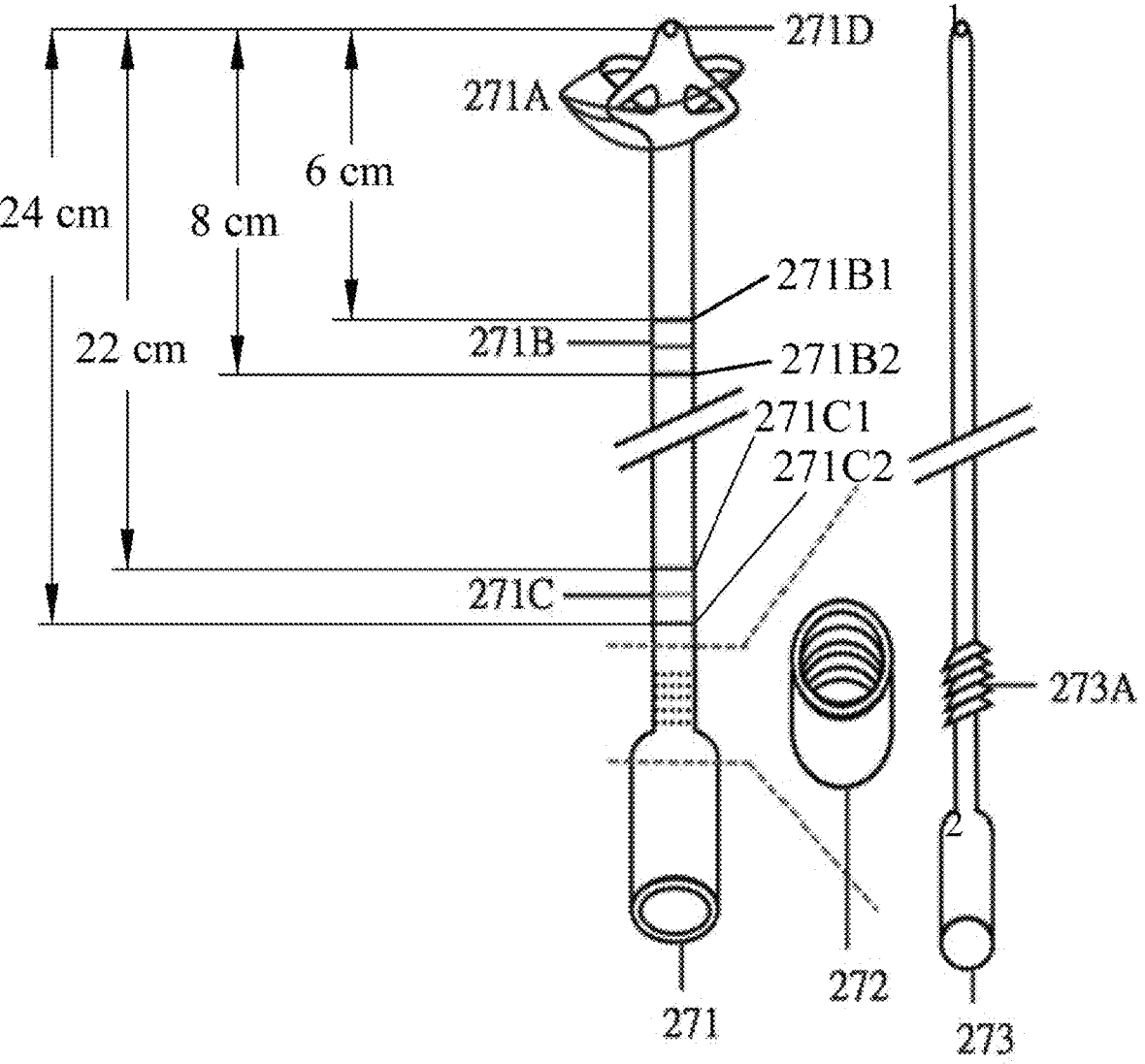
FIG. 20 illustrates an abbreviated whole length of separated internal soft stylet and external catheter of the balloon-free self-retainable thread-able externally calibrated urethral catheter, with a mechanism of holding them together via a distal nut-and-bolt mechanism close to the distal opening, according to one embodiment of the present invention.

Due to the different urethral lengths in men versus women, men have separate blue ruler markings. The length from the proximal tip to the first male ruler markings 271C1 is 22 cm [2 cm winged portion length+average male urethral length of 20 cm]; Length from proximal tip to third male ruler markings 271C2 is 24 cm [for older men with possibly longer prostate urethra and/or significant intravesical growth; warning of absolutely enough depth]. Females have separate red ruler markings (length from proximal tip to first female ruler markings 271B1 is 6 cm [2 cm winged portion+ average female urethral length of 4 cm], and length from proximal tip to third female ruler markings 271B2 is 8 cm [warning of absolutely enough depth](FIG. 20).

Another marker on the distal end 273 of the stylet may be included to inform the operator as to the readiness of stylet removal: a line that is initially hidden by catheter upon unpackaging but fully exposed once the locking mechanism is fully disengaged.

3. A single small hole 251C is formed at the tip of the catheter, and it's in continuity with the hollow inner lumen of the stylet 253B/253 to allow the passage of a guidewire, if one is used; in cases that this unpackaged novel catheter could be inserted along a guidewire in the bladder traveling out through the whole urethral lumen-similar concept in using a guidewire helping the proper insertion of a Council-tip urethral catheter.

Example 5

FIG. 20 illustrate a urethral catheter in accordance with an embodiment of the present disclosure. The major difference between this embodiment with Example 4 is that the "detachment mechanism" of the inner stylet and the outer winged-fenestrated balloon-free catheter is located at the external opening of the catheter. The "detachment mechanism" can be in the form of some easily detachable adhesive tapes or plastic wraps that hold the slightly more rigid inner soft stylet 273 and the outer winged-fenestrated balloon-free catheter 271 temporarily together to straighten the winged mechanism of the catheter from the manufacturing process, or it could be even a more proximally situated "nut and bolt" threads torqueing mechanism between the internal stylet 273 and the external catheter 271.

Similarly, an internal soft stylet 273 pushes and stream-lines the bladder end of this novel urethral catheter and makes the multi-winged mushroom portion 271A straightened in the pre-assembled unpackaged form; ready for use. This makes the insertion of such urethral catheter easily as current standard urethral catheter insertion (without or with the help of a guidewire). Once the catheter 271 is in correct position (as hinted by the external ruler markings in Example 4 mentioned above), the "detachment mechanism" of the bolt 273A and the nut 272 of the inner stylet (located at the external opening of the catheter) is to be activated; and the inner soft stylet 273 is pulled out while leaving the outer winged-fenestrated balloon-free urethral catheter in place; this will activate the multi-winged mechanism of the winged-fenestrated balloon-free urethral catheter, to be snugly positioned at the bladder neck.

Many fine details of this embodiment are the same as those in Example 4, like the inner central lumen and proximal end hole 271D for the guidewire; ruler markings 271B and 271C on the external surface of the urethral catheter; and also the prerequisite nature of the soft materials.

Example 6

Figure 21:
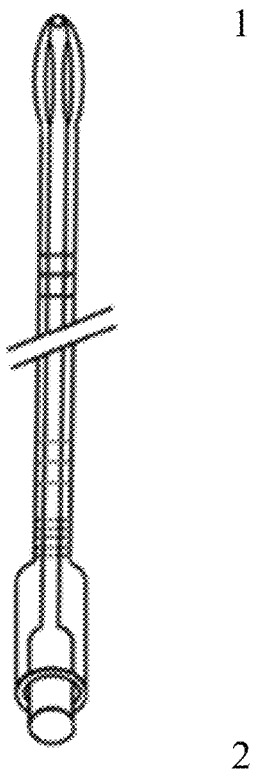
FIG. 21 illustrates a side view of assembled internal soft stylet and external catheter (FIG. 20), according to one embodiment of the present invention.
Figure 23:
FIG. 23 shows a schematic diagram of the Lotus catheter.
Figure 24:
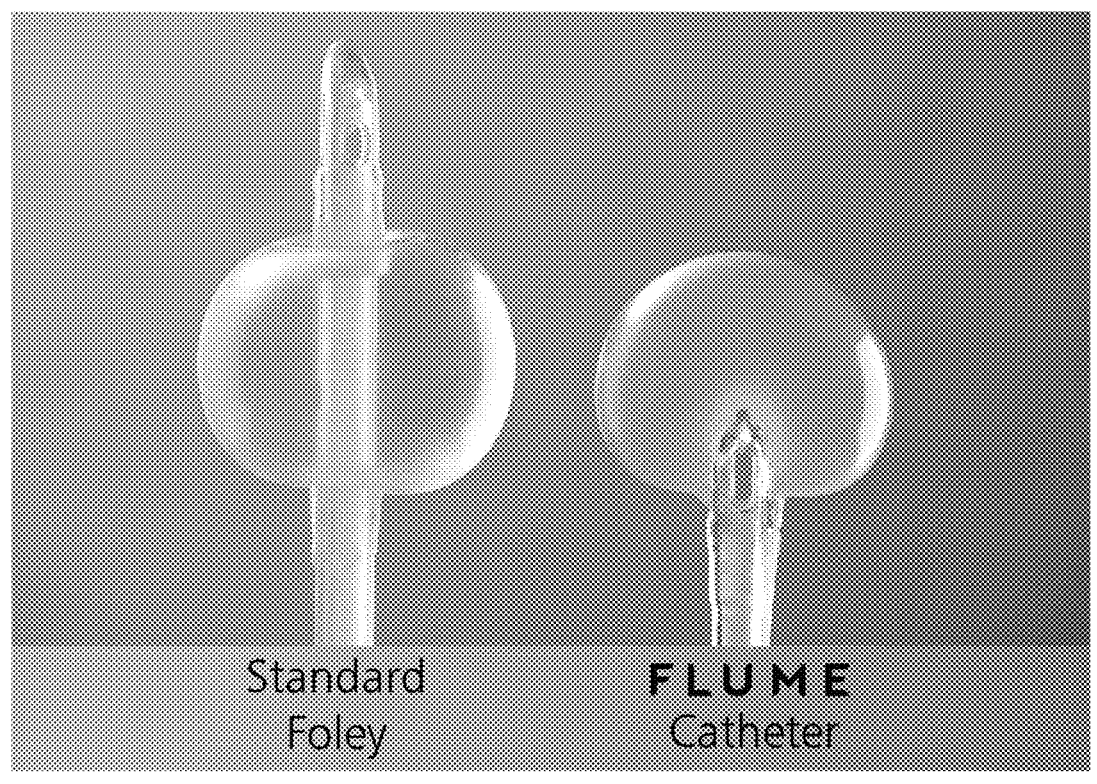
FIG. 24 shows a schematic diagram of the Flume catheter.

FIG. 21 illustrates a urethral catheter in accordance with an embodiment of the present disclosure. Example 6 is very similar to Example 5 with the feature that some "click and lock" mechanism (like the seat-belt), or snap-on closing mechanism is formed at the external opening of the stylet and catheter so that the winged fenestrations of the external catheter could be straightened into stream-line design with a longer internal stylet.

Example 7

Characteristics of Coating Materials:
1. When the urethral catheter is introduced into the urethra, the covering material has transitional water proof properties and binds the mushroom-like winged portion at the front end, forming a straight tube shape in which the front end remains unexpanded. Therefore, the front end of the urethral catheter can be passed smoothly through the urethra and into the bladder from the bladder neck.

2. When the front end of the urethral catheter enters the bladder, the covering material is infiltrated by urine at an appropriate time and ruptures, no longer binding the mushroom-like winged portion at the front end and allowing it to expand. Therefore, the front end of the urethral catheter can be hung on the bladder neck and fixed, and urine can flow into the urethral catheter through the front opening of the urethral catheter and then be discharged from the body.

Preparation of amphiphilic water-proof emulsion characteristics of coating materials: When the urethral catheter is introduced into the urethra (usually about 15 seconds to 4 minutes), the coating material prepared by using the amphiphilic water-proof emulsion of the present invention has a short-term water-proof function. When the coating material enters the bladder, it will dissolve, rupture or decompose into small fragments after being soaked in urine for a long time (usually about 4 to 20 minutes).

Composition of Amphiphilic Water-Proof Emulsion:
1. Emulsion polymerization is used to prepare an amphiphilic latex particle solution that has both hydrophilic and lipophilic properties.
2. Hydrophilic and lipophilic monomers are used as follows. Lipophilic monomers: methyl methacrylate, ethyl methacrylate, butyl methacrylate, methyl acrylate, butyl acrylate, 2-ethylhexyl acrylate, lauryl acrylate, styrene, vinyl acetate, vinyl chloride, vinyl acrylonitrile, glycidyl methacrylate, maleic anhydride, 2-hydroxyethyl methacrylate, 2-vinyl pyridine, 4-vinyl pyridine, and dibutyl itaconate. Hydrophilic monomers: acrylic acid, methacrylic acid, itaconic acid, 2-hydroxyethyl methacrylate, 4-hydrobutyl acrylate, sodium styrene sulfonate, vinyl pyrrolidone, acrylamide, and 2-methylpropenoic acid.

Synthetic Steps for Preparing Amphiphilic Water-Proof Emulsion

Figure 25:
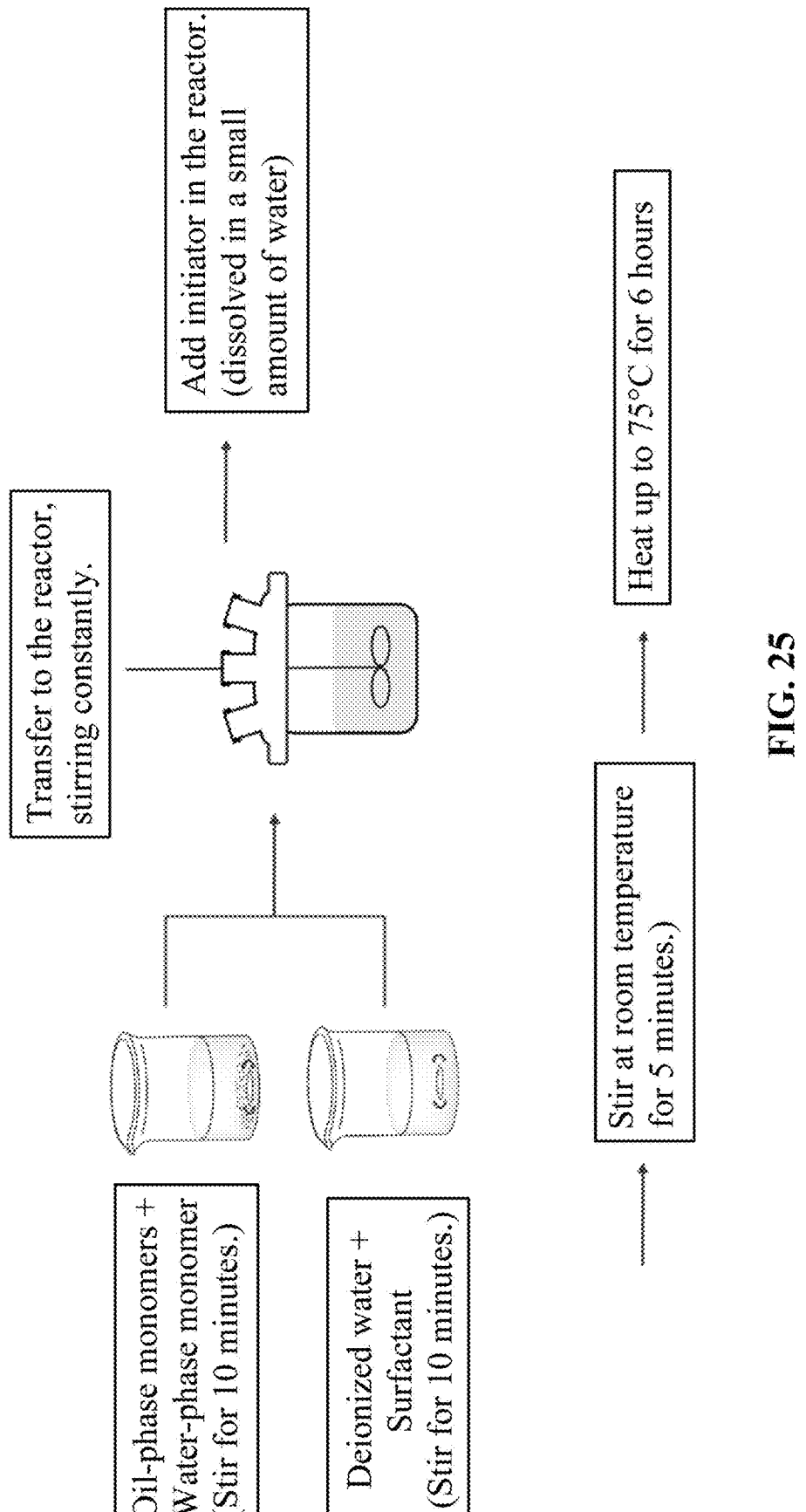
FIG. 25 is an experimental flow chart for the synthesis of amphiphilic water-proof emulsion.

1. As shown in FIG. 25, first the hydrophilic monomer (such as itaconic acid) and the lipophilic monomer (such as methyl methacrylate, lauryl acrylate, and dibutyl itaconate) were mixed and stirred evenly. 2. An emulsifier (such as sodium dodecyl sulfate) was dissolved in water. 3. The evenly mixed monomer and emulsifier solution were added into the reactor and stirring was continued. 4. After adding the initiator (such as potassium persulfate) into the reactor, the reaction mixture was stirred at room temperature for 5 minutes, followed by heating to the reaction temperature (for example: 75° C.). 5. After 6 hours of reaction, the amphiphilic water-proof emulsion is completed.

The material ratios of the amphiphilic water-proof emulsion synthesis are shown in Table 2 below.

TABLE 2

| | Formulation ratio | |
| --- | --- | --- |
| | 0.325/0.325/0.35 | 0.3/0.3/0.4 |
| Water-phase monomer (wt %) | 10% | 10% |
| Oil-phase monomer (wt %) | LA 29.25% DBIA 29.25% MMA 30.5% | LA 27% DBIA 27% MMA 36% |
| Surfactant (wt %) | SDS 2.5% | SDS 2.5% |
| Initiator | KPS 1% | KPS 1% |

Steps to Prepare Coating Materials:
1. Additives and thickeners such as polyvinyl alcohol PVA (0 wt % to 70 wt %), PEG4000 (0 wt % to 50 wt %), glycerol (0 wt % to 40 wt %), gelatin (0 wt % to 70 wt %), gum arabic (0 wt % to 70 wt %) were added as uniformly mixed with water in a specific ratio. 2. The amphiphilic water-proof emulsion (1 wt % to 100 wt %) was evenly mixed with the above solution. 3. Dip coating or blade coating was used to coat a solution with uniform thickness on the substrate or dip mandrel. 4. Drying was performed in an oven at 60° C. for more than one hour to dry into coating material. 5. Coating was repeated on the coating material as needed until thickness requirements were met. 6. The dried coating material was removed from the base material or dipped mandrel, and stored in isolation from moisture to obtain the finished product.

Formulation Ratio for Preparing Coating Materials:

The formulation solution of PVA:PEG4000:amphiphilic water-proof emulsion=14%: 1%: 3% (wt %) is called A. Formulation ratios are shown in Table 3.

an external adhesive or a wrapping material, wherein the external adhesive or the wrapping material wraps the proximal flexible mushroom-like winged end of the catheter to keep the proximal flexible mushroom-like winged end in a straight streamline form;

wherein the proximal flexible mushroom-like winged end conforms longitudinally when force of the stylet is applied, and forms a contour with its diameter larger than an outer diameter of the catheter when the force of the stylet is not applied, the external adhesive or the wrapping material is a water-soluble coating or a water-soluble capsule shell made of water-soluble materials, and the water-soluble coating or the water-soluble capsule shell comprises a formulation solution and the formulation solution comprises a water-proof emulsion.

TABLE 3

| Formulation ratio (A:glycerol) | 20:0 | 20:1 | 30:2 |
|---|---|---|---|
| thickness (μm) | 100 | 200 | 160 |
| PVA:PEG4000:amphiphilic water-proof emulsion:glycerol (wt %) | 78%:5%:17%:0% | 60.5%:4.5%:13.2%:21.8% | 56.6%:4.1%:12.1%:27.2% |
| Swelling time | 2 min 13 s | 6 min | 4 min |
| Dissolved time | 27 min | 18 min | 16 min |
| Formulation ratio (A:glycerol) | 20:2 | 20:3 | 20:4 |
| thickness (μm) | 160 | 180 | 160 |
| PVA:PEG4000:amphiphilic water-proof emulsion:glycerol (wt %) | 50.2%:3.6%:10.7%:35.5% | 42.6%:3%:9%:45.4% | 36.9%:2.6%:7.9%:52.6% |
| Swelling time | 3 min 30 s | 1 min | 30 s |
| Dissolved time | 13 min | 11 min | 10 min |

Best Performance Example

The best coating material ratios at present are 50.2% PVA, 3.6% PEG4000, 10.7% amphiphilic water-proof emulsion and 35.5% glycerol. 3 layers were repeatedly coated to create a coating material with a thickness of 160 m to 200 m.

In summary, through various experiments and the structural configuration, the balloon-free, self-retainable and threadable urethral catheter of the present invention can improve the efficiency of urine discharge from the body and reduce possible side effects, such as urinary retention, infection, urinary crystal precipitation, stone formation and irritation to the posterior wall of the bladder. If the patient accidentally pulls out the urethral catheter, the urethral catheter of the present invention can also reduce urethral trauma.

Although the present invention has been described with reference to the preferred embodiments, it will be apparent to those skilled in the art that a variety of modifications and changes in form and detail may be made without departing from the scope of the present invention defined by the appended claims.

What is claimed is:

1. A balloon-free, self-retainable and threadable urethral catheter, comprising:

a catheter, including a proximal flexible mushroom-like winged end and a distal end relative to the proximal flexible mushroom-like winged end, wherein the catheter has a hollow inner lumen between the proximal flexible mushroom-like winged end and the distal end;

a stylet movably inserted into the hollow inner lumen of the catheter from the distal end; and 2. The balloon-free, self-retainable and threadable urethral catheter according to claim 1, wherein the water-proof emulsion consists of a hydrophilic monomer and a lipophilic monomer.

3. The balloon-free, self-retainable and threadable urethral catheter according to claim 1, further comprising a locking mechanism, wherein the locking mechanism includes a threaded nut and a bolt segment matching the threaded nut, and the bolt segment is disposed on the stylet.

4. The balloon-free, self-retainable and threadable urethral catheter according to claim 1, wherein a small hole is formed at the proximal flexible mushroom-like winged end, and the small hole and the hollow inner lumen form a continuous space to allow a guidewire to pass through.

5. The balloon-free, self-retainable and threadable urethral catheter according to claim 1, wherein the distal end is formed with an external opening, the balloon-free, self-retainable and threadable urethral catheter further comprises a detachment mechanism, and the detachment mechanism is located at the external opening.

6. The balloon-free, self-retainable and threadable urethral catheter according to claim 1, wherein the proximal flexible mushroom-like winged end includes a multi-winged mushroom portion, the stylet pushes and streamlines the catheter and makes the multi-winged mushroom portion straightened in a pre-assembled unpackaged form.

7. The balloon-free, self-retainable and threadable urethral catheter according to claim 1, wherein the stylet has a proximal tip that meets the proximal flexible mushroom-like winged end of the catheter when inserted into the hollow inner lumen of the catheter.

8. The balloon-free, self-retainable and threadable urethral catheter according to claim 1, wherein the catheter further includes a ruler marking disposed on the catheter, the ruler marking includes a male ruler marking and a female ruler marking respectively, and the ruler marking is used to notify users of different genders as to length of the catheter already inserted into body.

\*  \*  \*  \*  \*